US005884846A

United States Patent [19]

Tan

[11] Patent Number: 5,884,846

[45] Date of Patent: Mar. 23, 1999

[54] PNEUMATIC CONCENTRIC NEBULIZER WITH ADJUSTABLE AND CAPILLARIES

[76] Inventor: Hsiaoming Sherman Tan, 32 Whites Ave. #8802, Watertown, Mass. 02172

[21] Appl. No.: 933,602

[22] Filed: Sep. 18, 1997

Related U.S. Application Data

[60] Provisional application No. 60/026,338 Sep. 19, 1996.

[51] Int. Cl.[6] .......... A61M 11/06

[52] U.S. Cl. .......... 239/338; 239/346; 239/418; 239/424; 128/200.21

[58] Field of Search .......... 239/311, 314, 239/318, 338, 340, 346, 418, 423, 424, DIG. 7, 433, 600; 261/78.2; 128/200.21

[56] References Cited

U.S. PATENT DOCUMENTS

| | | | |
|---|---|---|---|
| 3,264,683 | 8/1966 | Lloyd | 239/338 |
| 3,552,657 | 1/1971 | Chisholm | 239/424 |
| 4,125,225 | 11/1978 | Venghiattis | 239/346 |
| 4,206,160 | 6/1980 | Suddendorg et al. | 239/338 |
| 4,880,164 | 11/1989 | Noordermeer | 239/423 |
| 5,411,208 | 5/1995 | Burgener | 239/8 |
| 5,464,157 | 11/1995 | Bourdoulous et al. | 239/424 |

*Primary Examiner*—Andres Kashnikow
*Assistant Examiner*—Lisa Ann Douglas
*Attorney, Agent, or Firm*—Louis J. Franco

[57] ABSTRACT

A concentric nebulizer having applicability in inductively coupled plasma spectrometry is disclosed. The device features a nebulizer tube with a tapered front open end and mechanism for removing, replacing, and adjusting the position of central sample capillaries with respect to the opening in the front end to adjust such parameters as gas pressure, sample flow rates, and aerosol formation over a wide range. Devices constructed in accordance with the invention may operate at low gas pressure and are physically compatible to glass concentric nebulizers.

18 Claims, 5 Drawing Sheets

PNEUMATIC CONCENTRIC NEBULIZER WITH ADJUSTABLE AND CAPILLARIES

PRIORITY BASED ON PREVIOUSLY FILED PROVISIONAL APPLICATION

This non-provisional application is based on a provisional application filed on Sep. 19, 1996 and assigned Ser. No. 60/026,338, and claims the benefit of the filing date of the provisional application. To the extent necessary for clarification and explanation of the invention, the entire text and drawings of the provisional application are incorporated into this non-provisional application by reference.

FIELD OF THE INVENTION

This invention relates generally to nebulizers used for the introduction of samples to be analyzed using inductively coupled plasma spectrometry (hereinafter, ICP spectrometry), and more particularly to an improved pneumatic concentric nebulizer with a central sample capillary which, among other features, permits a user of the device to adjust the position of the central capillary and remove and replace capillaries within the device.

BACKGROUND OF THE INVENTION

Sample introduction systems have been the weak link of ICP spectrometry. In ICP spectrometry, a liquid sample solution typically is converted into a form of aerosol, carried by an inert gas such as argon, and then injected into an ICP spectrometer for analysis. The converting of the liquid sample is normally accomplished through use of a nebulizer. Prior to the aerosol's being injected into the ICP spectrometer, large droplets of sample are removed by means of a spray chamber, for example. Only the smaller, useful particles are introduced into the ICP spectrometer. "Nebulization efficiency" is a relevant factor in this process and is defined as the amount of sample introduced into the ICP spectrometer after the removal of large droplets (i.e., useful aerosol) divided by the total amount of sample initially delivered to the nebulizer. Problems associate with low nebulization efficiency and current devices, which are generally of low nebulization efficiency, are unsuitable for analysis of samples introduced over a wide range of flow rates, and often require the use of a high pressure pump or other mechanism to introduce an adequate volume of sample for experimental purposes. In general, there are two types of sample introduction systems, ultrasonic nebulizers and pneumatic nebulizers. Less common devices include thermospray and direct injection nebulizers. A brief discussion of various relevant nebulizers is presented below. A more detailed and thorough discussion of various nebulizers and of nebulization generally is presented in the specification and drawings of U.S. Pat. No. 5,411,208 issued to John A. Burgener on May 2, 1995 and the text and drawings of that patent are incorporated herein by reference for purposes of clarification where necessary.

Ultrasonic nebulizers typically offer 10 times the nebulization efficiency of pneumatic nebulizers. However, ultrasonic nebulizers are more complicated to operate than pneumatic nebulizers. Also there have been reports regarding interferences due to nebulization desolvation for the ultrasonic nebulizer. "Nebulization desolvation" is a process used to remove water vapor and large particles prior to aerosol injection into the ICP spectrometer. Less complicated pneumatic nebulizers can be classified as cross-flow and concentric nebulizers. Among all sample introduction systems, glass concentric nebulizers are the most popular due to their simplicity in design and operation. The current invention relates closely with glass concentric nebulizers.

The basic operating principle of a glass concentric nebulizer is simple and is explained with the aid of FIGS. 1 to 3. FIG. 1 depicts the structure of a typical glass concentric nebulizer. The nebulizer is a single piece formed from glass. The nebulizer has an elongated hollow main tube with a rear end and a front end. The front end is tapered down in roughly the shape of a cone and terminates in an opening. Coming off the side of the main tube is a gas tube for feeding gas into the main tube for expulsion through the opening in the front end of the main tube. The main tube carries in its interior an integrally formed central capillary which extends from the rear end of the main tube to the front open end of the main tube and is aligned in concentric fashion with respect the main tube. The outside of the central capillary and the inside of the rear end of the main tube are sealed together as shown in FIG. 1 so that gas being fed into the main tube from the gas tube cannot escape through the rear end of the main tube, but instead, is forced to escape through the opening in the front end of the main tube. The inner diameter of the main tube is larger at all points along its length than the outer diameter of the central capillary so that gas can escape through the space between the two at the front end of the main tube. The space between the capillary and the front end of the main tube is referred to as the gas annulus.

In operation, a liquid sample is fed into the rearward end of the central capillary and is expelled through the forward end of the capillary. At the same time, gas is fed into the main tube from the gas tube. The liquid sample may be moved through the central capillary by free suction created by the partial vacuum at the forward end of the capillary due to the rapidly exiting gas or by pumping it into the rearward end of the capillary or both. The sample flow rate created by free suction at given gas flow rates is known as the "natural aspiration rate." As the liquid exits the capillary, it interacts with the gas being expelled under pressure through the gas annulus in the main tube and forms an aerosol. Typically, inert gases such as argon are used, but any gas may be used that is consistent with protocol for a particular experiment. As can be seen in FIG. 1, the forward end of the capillary cooperates with the opening in the main tube to form a nozzle. The translational position of the capillary's forward end with respect to the opening in the main tube is critical in aerosol formation. There are typically three configurations for these types of nozzles. In one configuration, the capillary's forward end extends outside the glass tube, beyond the opening in the main tube. In a second configuration, the capillary's forward end is flush with the opening in the glass tube. In a third configuration, the forward end of the capillary is recessed with respect to the opening in the glass tube. It is easy to appreciate based on how these nebulizers are manufactured that the nozzle configuration is fixed permanently for any single glass concentric nebulizer. Not only is the position of the forward end of the capillary fixed with respect to the opening in the front of the main tube, but other parameters critical to aerosol formation are fixed as well such as the inner and outer diameters of the central capillary, the inner diameter of the main glass tube at its front end opening, the size of the opening at the front end of the main tube, and the cross-sectional area of the gas annulus. All of these parameters play a central role in the formation of aerosol and, because they are fixed for any given single-piece nebulizer, frequent changing of entire nebulizers during experimentation is necessary where different analytical applications (e.g. different flow rates) are desired.

At present, there are generally two types of glass concentric nebulizers, one for regular sample flow rates and the other for micro-volume sample flow rates. “Regular sample flow rate” is on the order of milliliters of sample per minute (mL/min) flowing through the capillary while “micro-volume sample flow rate” is on the order of microliters of sample per minute ($\mu$L/min) flowing through the capillary. For best results, the sample flow rate used should be close to the natural aspiration rate. If the sample flow rate is much lower than the natural aspiration rate, pulsation in nebulization occurs due to the sudden burst of sample aerosol created by free suction which is followed by a bubble at the capillary tip. This phenomenon is referred to as the “nebulization starvation effect.” For example, the regular MEINHARD glass concentric nebulizer (FIG. 2) passes anywhere from 0.5 to 2 mL/min. of sample through its capillary at the natural aspiration rate and the MEINHARD glass concentric High Efficiency Nebulizer (FIG. 3) typically passes less than 100 $\mu$L/min of sample through its capillary at the natural aspiration rate under typical conditions. These two nebulizers are almost identical except for the nozzle opening and the capillary. The inner diameter of the sample capillary is the primary factor that determines the sample flow rates of the two nebulizers. A regular flow rate device such as that in FIG. 2 possesses a capillary with a larger inner diameter ranging from 220–320 plus microns as compared to approximately 100 microns for the micro-volume device of FIG. 3. Because of their larger capillary inner diameters, regular concentric nebulizers are not suitable for micro-volume sample analysis due to the “nebulization starvation effect” under the typical operating conditions. Relatedly, use of the micro-volume devices at an increased sample flow rate (e.g., greater than 0.5 mL/min) is difficult because the reduced inner diameter of the capillary limits the volume of sample that can flow through the capillary per unit time. To increase the sample flow rate through these micro-volume nebulizers, a high pressure pump is required to pump the sample through the capillary. However, use of a low pressure sample pump (e.g., a peristaltic pump) is preferable in ICP spectrochemical analysis because it allows easy cleaning and rapid sample switch over.

Another difference between the regular and high efficiency nebulizers is the gas operating pressure. Because the gas annulus for the high efficiency nebulizer is typically on the order of 5 times smaller in area than that of the regular concentric nebulizer, the gas operating pressure is about 180 psi as compared to 20 to 60 psi for the regular nebulizer. The nebulizing gas flow rate for both nebulizers under normal conditions is around 1 liter per minute. Because of the small gas annulus, higher pressure is needed to force gas through the gas annulus of the high efficiency nebulizer than the gas annulus of the regular nebulizer. Again, low operating pressure is desirable for normal analytical applications.

As for sample flow rates, to pump sample through the capillary of a regular nebulizer at a rate of 1–2 mL/min, only a low pressure pump (e.g. a peristaltic pump) is required. However, for a high efficiency nebulizer, a high pressure pump is required due to the smaller inner diameter of the sample capillary.

In the cases of both gas and sample solution, low operating pressure is preferred because it makes conducting experiments simpler and safer.

An alternative to the nebulizers currently used to analyze samples at different sample flow rates is to use just one nebulizer with a replaceable capillary and a replaceable main tube with a tapered open front end. This is not possible with the glass concentric nebulizers commonly in use because the entire device is sealed by glass-blowing various components together to form a single, inseparable article of manufacture. To remove a capillary from the single piece glass concentric nebulizer would require the destruction of the entire device. Similarly, replacing other individual parts of these nebulizers, such as the gas tube, is not possible for the same obvious reason. Presented below are the details of the present invention which, among other things, permit a user to change capillaries, adjust the position of capillaries with respect to the opening at the front end of the glass tube, and interchange the functional equivalent of the main glass tubes to vary the size of the front end opening.

Other, less relevant, devices related to the field of the current invention include the micro concentric nebulizer and the oscillating concentric nebulizer.

The micro concentric nebulizer, developed at CETAC Technology, Inc. (Omaha,Nebr.), is made of various materials, PVDF(Kynar), sapphire, polyimide, PEEK, and TEFLON among them. It is also a concentric nebulizer that applies principles of pneumatic nebulization. The nebulizer is designed for low sample flow rates similar to those of the high efficiency nebulizer discussed earlier with the exception that the device can be operated at reduced gas pressure. Because the outer diameter of this nebulizer body is much greater than that of the glass concentric nebulizer, this nebulizer requires its own mount to the spray chamber of ICP. In addition, the CETAC device does not permit a user to simply interchange capillaries of different inner and outer diameters nor does it allow a user to vary the gas pressure over a continuum because it lacks a tapered front end in which the position of the capillary with respect to the front end may be adjusted.

The oscillating capillary nebulizer, developed at Georgia Institute of Technology (Atlanta, Ga.), is made by forming a nebulizer nozzle with a pair of chromatograph columns. The operating principle of this nebulizer combines pneumatic effect and center capillary oscillation. Oscillation occurs when sample and gas are introduced and is in the range of 200 Hertz to 1400 Hertz. The oscillation begins in the inner capillary which in turn induces oscillations in the outer capillary. Typical inner diameters for the inside and outside capillaries are 50 microns and 250 microns, respectively. In the device as actually constructed, the outer diameters would typically be 142 microns and 440 microns, respectively. The positions of the capillaries are fixed by using stainless steel nuts and PEEK tubing ferrules. The entire nebulizer body is constructed of stainless steel. The nozzle configuration (i.e., the position of the inner capillary with respect to the outer capillary) is adjusted through a rotating connecting ring. An O-ring seal is applied in the connection. The preferable nozzle configuration for this nebulizer is to have the inner capillary extend outside of the outer capillary. This design allows replacement of various parts including the capillary pair for the nozzle. However, because the outer capillary is too small and not as strong as the outer shell of the main tube of a glass concentric nebulizer, a special mount is also required for using the Georgia Institute of Technology nebulizer with a common spray chamber of an ICP spectrometer. In addition, because this device uses two commercially available capillaries for nozzle fabrication, the gap for the gas passage (gas annulus) between two capillaries can not be varied continuously because the capillaries have constant radii over their entire lengths. The ability to vary the ratio of the radii is necessary to obtain different nebulizing gas pressures. For example, for a given sample capillary, a continuous increase of the inner diameter of the outside capillary (or main tube) results in a gradual decrease of nebulizing gas pressure and vice versa. This adjustment capability is preferable to operate nebulizers at different gas pressures. As will be seen, the present invention achieves this feature of variable gas pressure by permitting linear movement of the central capillary within a tapered (conic) main tube front end which varies the ratio of the inner diameter of the main outer tube and the outer diameter of the central capillary.

SUMMARY OF THE INVENTION

It is therefore a primary object of this invention to provide an improved device which pneumatically converts sample solution into a form of aerosol for analytical purposes and applications.

It is a further object of this invention to provide a concentric nebulizer which allows easy replacement of various parts including central capillaries of different inner and outer diameters and main nebulizer tubes with different inner diameters and front end opening sizes so that wide ranges of sample flow rates and various gas pressures can be attained by a single device.

It is still another object of this invention to provide a concentric nebulizer with a means for adjusting the linear position of the sample exit end of any given central capillary with respect to the opening at the end of the tapered portion of the main nebulizer tube so that gas pressure can be varied.

It is still a further object of the invention to provide a device that is physically compatible and interchangeable with the glass concentric nebulizers presently in use for ICP instrumentations so that it may be operated at low gas pressure and be adapted to any ICP spray chamber and a regular low pressure pumping device may be used for sample solution transfer and introduction through the central capillary.

This invention results from the realization that there is a great need for a concentric nebulizer that allows a user to quickly, conveniently, and inexpensively vary the parameters that control sample flow rate, gas pressure, and aerosol formation. The invented apparatus, in the broad sense, includes a housing with a hollow chamber therein and a rear end and front end. Communicating with the chamber are three openings; a first one at the front end, a second one at the rear end, and a third one which may be situated anywhere on the housing as long as it is in fluid communication with the chamber within the housing. The front end of the housing is provided with nebulizer tube sealing means to removably receive and sealably engage the rear end of a nebulizer tube which has an interior surface or wall, a rear end, and a front end. The interior surface of the front end of the nebulizer tube is tapered downward and terminates in an orifice. The tapered surface resembles a cone and the orifice is where the point of the cone would be if the front end were closed. A channel passes through the entire length of the nebulizer tube, running from and communicating with the orifice at the tube's front end to the rear end of the tube. The method or hardware used to detachably mount and sealably engage the nebutizer tube at the front end of the housing is immaterial so long as a gas tight seal is formed between the nebulizer tube and the housing when the device is in use, the nebulizer tube is removable without the need for damaging it or the housing, and the channel within the nebulizer tube communicates with the chamber within the housing.

At the rear end of the housing is an opening through which a sample capillary is removably received and sealably engaged by capillary sealing means which sealing means are proximate to the rear end of the housing. The capillary sealing means are movable between an open position and a sealing position for slidably and removably receiving, and selectively sealably engaging, capillaries received through the opening at the rear of the housing. When the capillary sealing means are in the open position, a capillary can be inserted, removed, or have its position linearly adjusted within the housing. When the capillary sealing means are in the closed position, there is a gas-tight seal between the housing and the capillary inserted therein. The capillary sealing means are capable of receiving and selectively sealably engaging capillaries of various inner and outer diameters so that sample flow rates and gas pressures can be varied. The opening through which the capillary is received should be aligned with the orifice at the front end of the nebulizer tube when the nebulizer tube is properly installed on the housing so that the front end of a capillary being installed in the device may be put into proximity with and pass through (if desired) the orifice at the nebulizer tube's front end. Aligning the opening at the rear end of the housing with the orifice at the front end of the housing is certainly the simplest and most efficient means for achieving the desired result, but it is not the only means. Persons of ordinary skill in the art could fashion alternative ways of accomplishing the same objective. For example, the inside of the housing could be provided with a guide or series of guides for directing the advancing front end of the capillary to a position proximate to the front open end of the nebulizer tube and perhaps, under some circumstances, such a system would be desirable, if not necessary. Such embodiments would certainly be within the scope and spirit of the present invention as all that is necessary regarding the capillary as it relates to the present invention is that it can be removably received into the device, sealably engaged with a gas tight seal therearound during use of the device, have the position of its front end adjusted and held in place with respect to the orifice at the front end of the nebulizer tube, and be readily removed when replacement of the same is desired. When in use, the rear end of the capillary is attached to a source of fluid sample (most commonly liquid) which sample is fed through the channel within the capillary by pumping or free suction or both.

The third opening in the housing is a gas entrance opening and is designed for removable and sealable engagement with a source of gas. For example, a gas line or hose would run from a tank or other source at one end, while its other end could be connected to the third opening in the housing in such a fashion that gas coming through the line and filling the chamber within the housing cannot leak through the point of connection between the gas line and the housing.

When the device is in use, gas is supplied to the chamber within the housing through the third opening in the housing while sample is ejected from the front end of the capillary which is in proximity with the orifice at the front end of the nebulizer tube. Because the housing is closed except for the three openings and there are gas tight seals at the rear end of the housing around the capillary, at the gas line connection, and between the rear end of the nebulizer tube and the opening at the front end of the housing, gas being fed into the chamber is forced to pass under pressure through the only opening that remains, the orifice at the front end of the nebulizer tube. There, the gas interacts with sample exiting the front end of the capillary and forms an aerosol.

As discussed above, when the user of the device wishes to vary parameters such as capillary internal or external diameters, nebulizer tube inner diameter, orifice size, and or gas annulus area, the appropriate parts may simply be removed and replaced. If all that is desired is to change the position of the front end of the capillary with respect to the orifice at the front end of the nebulizer tube, then the gas tight seal around the capillary at the rear end of the housing is simply loosened, the position of the capillary reset, and the seal re-tightened.

Among its many advantages, a device constructed in accordance with the present invention allows a user to analyze samples at various flow rates (e.g. 1.0 $\mu$L/min to 2.0 mL/min.) by permitting the user to interchange capillaries of different inner diameters on a single device. The changing of capillaries with similar inner diameters may also be done when the nebulizer malfunctions due to capillary defects. The nebulizer interchanges with a glass concentric nebulizer easily without any special mounting device. By facilitating linear movement of the front end of the capillary with respect to the tapered end of the nebulizer tube, the size of the gas annulus of the nebulizer can be adjusted continuously to obtain different nebulizing gas pressures. The nozzle may be configured to have any gas operating pressure along a range. For the most common applications, the pressure ranges from 30 to 60 pounds per square inch, for example. The nebulizer of the instant invention is easy to manufacture and all parts are inexpensive and readily available.

Instead of constructing the entire concentric nebulizer out of glass as the single-piece nebulizers are, the nebulizer can be constructed from any of several materials such as glass, polyetheretherketone (PEEK), stainless steel, brass, or any other material so long as any components of the device that come into contact with corrosive or otherwise reactive samples are chosen so as not to be damaged or destroyed by the chosen sample. In other words, the materials chosen for the parts which come into contact with sample solution should be impervious to chemical attack by such solution. Obviously, the chosen materials must also be strong enough to withstand gas pressures within the ranges required for ICP spectrometry. The nebulizer's main tube may be made by using a tapered tubing, preferably glass, with a small end orifice in combination with an untreated bare fused silica capillary column as a nebulizer capillary. The outside surface of the capillary may be coated with polyimide to enhance its physical strength and flexibility. The two aligned openings of a Tee "T" shaped union connector are used to assemble the tapered-tubing and the capillary together by using nuts and ferrules as described in greater detail infra. To properly connect the capillary to the nebulizer body, a piece of compressible tubing is needed as an additional ferrule or sleeve. One "T" opening or a side-arm tube extension is provided to facilitate the introduction of nebulizing gas. There are several advantages of this nebulizer over a glass concentric nebulizer. First of all, switchable capillaries of different inner diameters allow for analysis of samples at a much wider range of flow rates than is possible with a single, one-piece device. Different types of nebulizer nozzles may be obtained by adjusting the position of the capillary tip with respect to the tapered-tube end opening. Moreover, replacement of any individual part is made possible and simple. Furthermore, the nebulizer may be constructed from any number of materials. Finally, a regular pumping system (e.g. a peristaltic pump) is sufficient to fulfill the pumping needs for sample delivery.

It should be noted that, while throughout the description of prior related devices and the summary and detailed descriptions of this invention, various dimensions, flow rates and materials for construction have been stated, these figures and statements have been offered by way of example and should not be construed so as to limit the scope of the current invention which may operate well outside the given ranges or which may very well have applications outside ICP spectrometry altogether. For example, the concentric nebulizer of the current invention could be adapted for use as a painting nozzle where the chosen gas would be air supplied by a compressor and the sample would be paint.

DETAILED DESCRIPTION OF THE PREFERRED EMBODIMENT

Figure 1:
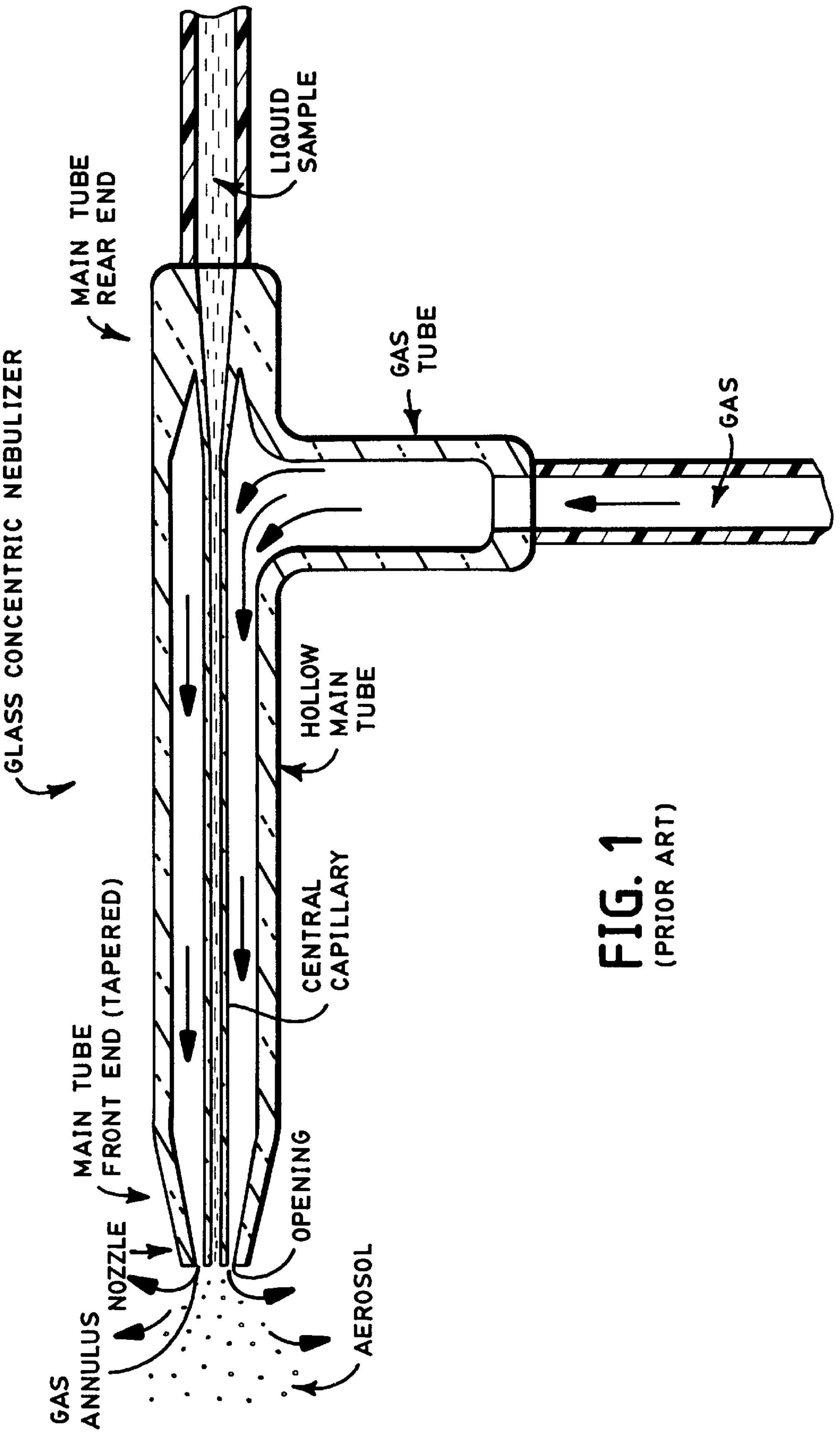
FIG. 1 (PRIOR ART)
FIG. 1 depicts a glass concentric nebulizer of the kind currently in common use.
Figure 2:
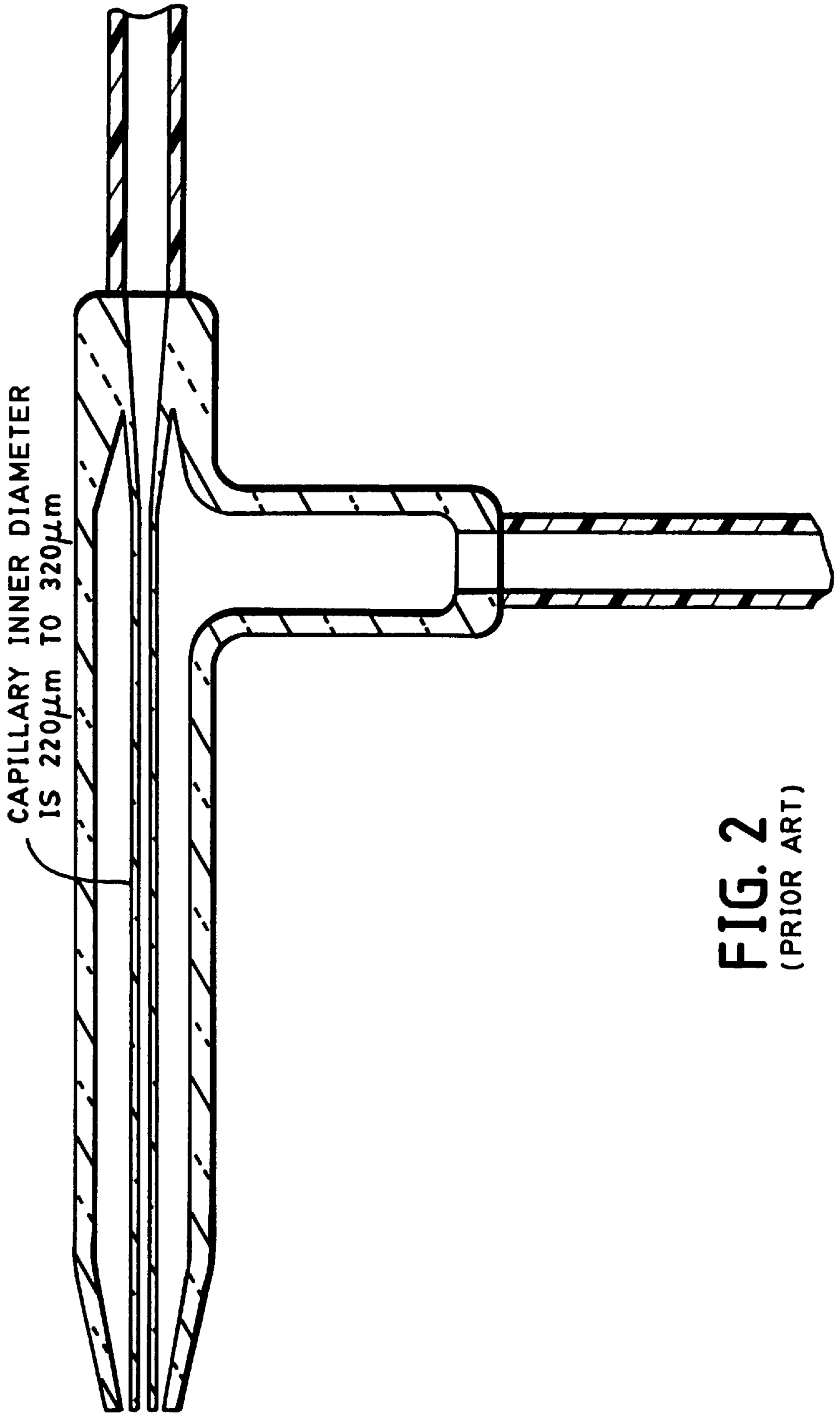
FIG. 2 (PRIOR ART)
FIG. 2 is a side, cross-sectional view of a typical regular glass concentric nebulizer.
Figure 3:
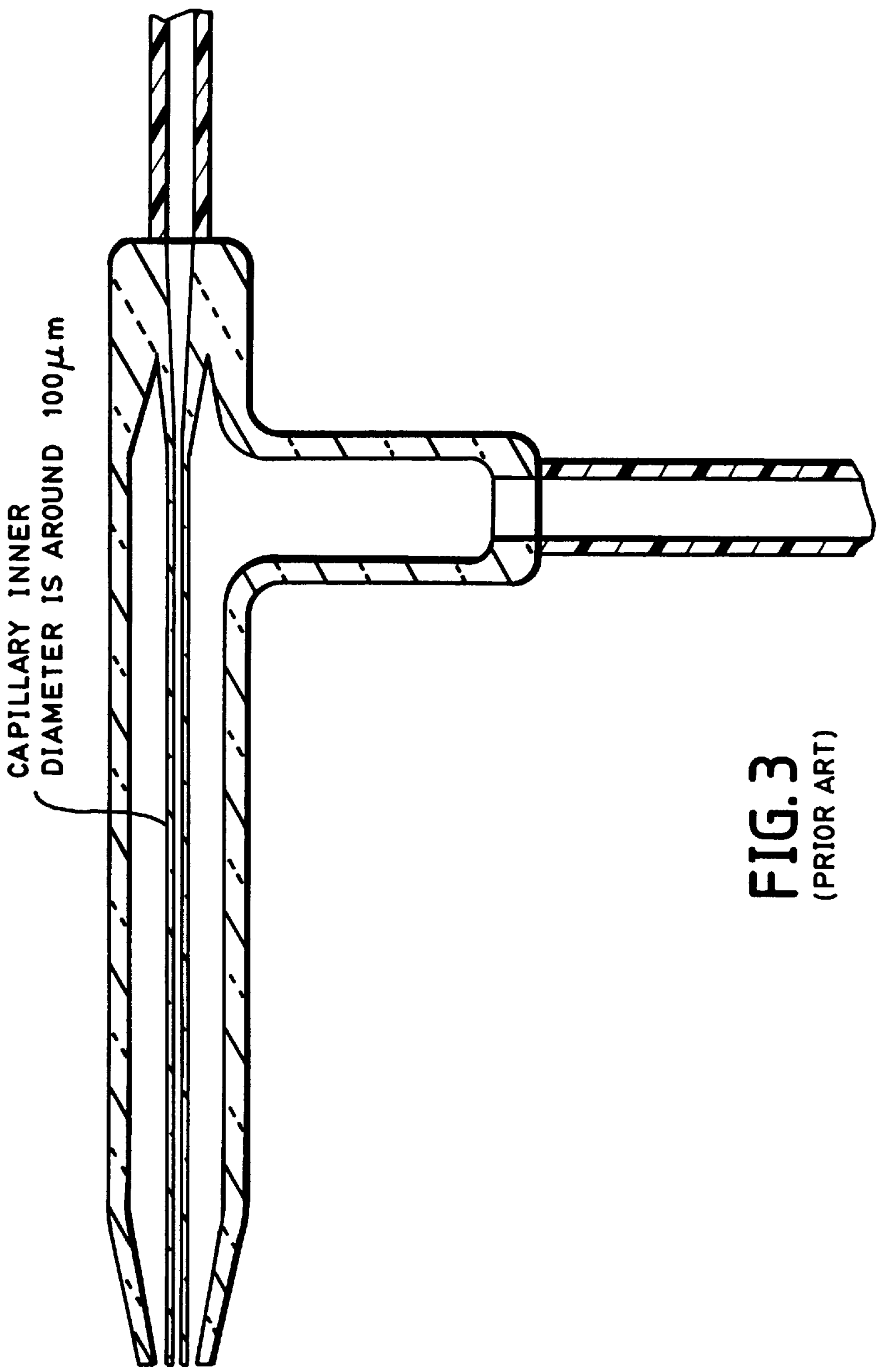
FIG. 3 (PRIOR ART)
FIG. 3 is a side, cross-sectional view of a typical high efficiency nebulizer.

The nebulizer according to a preferred embodiment of my invention comprises three main components (FIGS. 4, 4*a*, and 4*b*): A T-shaped central housing 100, a nebulizer tube 200, and a central capillary 300.

T-shaped central housing 100 comprises a tube 110 having a cylindrical interior wall 112, an exterior wall 114, a rear end 120, and a front end 130. A bore 140 extends from rear end 120 through front end 130. Rear end 120 contains a recessed capillary guide wall 122 which has a front face 124 and a rear face 125. Guide wall 122 extends radially inward from cylindrical interior wall 112 to a guide aperture 126. Guide aperture 126 extends through guide wall 122 from front face 124 to rear face 125 and is bounded by a cylindrical guide wall interior surface 127. The portion of tube 110 that extends behind rear face 125 of recessed guide wall 122 contains rear end internal threads 128 along interior wall 112. Front end 130 is provided with nebulizer tube sealing means to removably receive and sealably engage nebulizer tube 200. Front end 130 has a nebulizer seat 132, a nebulizer ferrule shoulder 134, and front end internal threads 136. Nebulizer tube 200, preferably constructed from glass, has an interior cylindrical surface 202, an exterior surface 204, a rear gas entrance end 210, and a forward gas expulsion end 220. Gas expulsion end 220 is tapered downward and terminates in an expulsion orifice 222. A channel 230 communicates with expulsion orifice 222 and extends rearward from expulsion orifice 222 through rear gas entrance end 210. Nebulizer tube 200 is further provided with a nebulizer ferrule 240 which is secured around exterior surface 204 so that it cannot readily slide along surface 204. Nebulizer ferrule 240 is made from a flexible material so that it can create a seal when deformed under pressure and then return substantially to its original shape (i.e., before compression) when pressure is removed therefrom. Nebulizer securing nut 246 is slidably received around exterior surface 204. To install nebulizer tube 200 into front end 130 of tube 110, rear gas entrance end 210 is inserted into front end 130 until rear gas entrance end 210 comes into contact with nebulizer seat 132 and nebulizer ferrule 240 comes into contact with nebulizer ferrule shoulder 134. To sealably secure nebulizer tube 200 in place, nebulizer securing nut 246, which has exterior threads 248, is threaded into front end internal threads 136 of front end 130 until nebulizer ferrule 240 is compressed between securing nut 246, ferrule seat 134, exterior surface 204 and interior wall 112 and a seal sufficient to prevent pressurized gas from leaking therethrough is created. A gas tight seal may also be created between rear gas entrance end 210 and nebulizer seat 132, but all that is required is a nebulizer tube sealing means to prevent gas from leaking at the junction between nebulizer tube 200 and front end 130.

Extending substantially perpendicularly from external wall 114 of tube 110 is a gas conduit 150. Gas conduit 150 has an open gas line receiving end 152, an open gas discharge end 153, an exterior wall 154, and an interior wall 155. A bore 160 extends through gas conduit 150 from gas line receiving end 152 to gas discharge end 153. Bore 140, extending through tube 110, and bore 160 cooperate to form cavity 162. Gas entrance conduit 150 is designed to receive and sealably engage gas line 500 through gas line receiving end 152. Gas line receiving end 152 has internal threads 154 along interior wall 155. A gas line ferrule shoulder 156 and a gas line seat 157 are formed within interior wall 155. Gas line 500 is hollow and carries gas from a tank or other source to gas conduit 150 and into cavity 162 and has an interior wall 502, an exterior wall 504, and a gas exit end 506. A gas line ferrule 520 is fitted around exterior wall 504 so that it cannot readily slide along exterior wall 504. Gas line ferrule 520 is designed to flex under pressure and then return substantially to its uncompressed shape once pressure is removed, so that it acts has a good seal but can be removed when desired. A gas line securing nut 530 is loosely fitted around exterior wall 604 so that it can freely slide along exterior wall 504 of gas line 500 and has external threads 532. To sealably secure gas line 500 within gas conduit 150, gas exit end 506 is inserted into gas conduit 150 via gas line receiving end 152 until gas exit end 506 comes into contact with gas line seat 157 and gas line ferrule 520 comes into contact with gas line ferrule shoulder 156. External threads 532 of gas line securing nut 530 are then threaded into internal threads 154 until a seal sufficient to prevent pressurized gas from leaking therethrough is achieved by the compression and deformation of ferrule 520.

Rear end 120 of tube 110 is adapted to receive central capillary 300 through guide aperture 126 in capillary guide wall 122. Central capillary 300 has a first sample intake port 302, a second sample exit port 304, an cylindrical inner wall 306, and a cylindrical outer wall 308. A sample channel 309 extends from first sample intake port 302 to second sample exit port 304. Outer wall 308 is provided with a cylindrical capillary compression sleeve 310 which fits snugly around outer wall 308. An inner capillary ferrule 312 and an outer capillary ferrule 314 are slidably received around compression sleeve 310. When installation of central capillary 300 is desired, nebulizer tube 200 should be properly installed first. To install central capillary 300, the end of capillary 300 having second sample exit port 304 is inserted into rear end 120, through guide aperture 126, and translated toward gas expulsion end 220 of nebulizer tube 200. When sample exit port 304 is at the desired proximity with respect to orifice 222, which is in alignment with guide aperture 126, inner and outer capillary ferrules 312 and 314 are compressed onto capillary compression sleeve 310 by threading capillary securing nut 320, which has external threads 322, into rear end internal threads 128 of tube 110 until capillary 300 cannot be translated forward or backward and a gas tight seal is formed at capillary guide wall 122 so that gas in cavity 162 cannot escape through guide aperture 126. To adjust the position of, or remove, central capillary 300, capillary securing nut 320 is threaded out of rear end internal threads 128 and outer ferrule 314 is loosened from inner ferrule 312 to allow inner capillary ferrule 312 to open and permit translational motion between inner capillary ferrule 312 and capillary compression sleeve 310. To fully understand how this compression is achieved, it should be noted in FIG. 4 that inner ferrule 312 has a conical outer surface so that as outer ferrule 314 is advanced in the forward direction by the tightening of capillary securing nut 320, the inner surface of inner ferrule 312 squeezes down on the outer surface of capillary compression sleeve 310. The inner surface of compression sleeve 310 is squeezed down onto the outer cylindrical wall 308 of capillary 300. Conversely, when securing nut 320 is loosened and outer ferrule 314 is moved in the rearward direction, inner ferrule 312 opens and releases its hold on compression sleeve 310.

Figures 4, 4A, 4B:
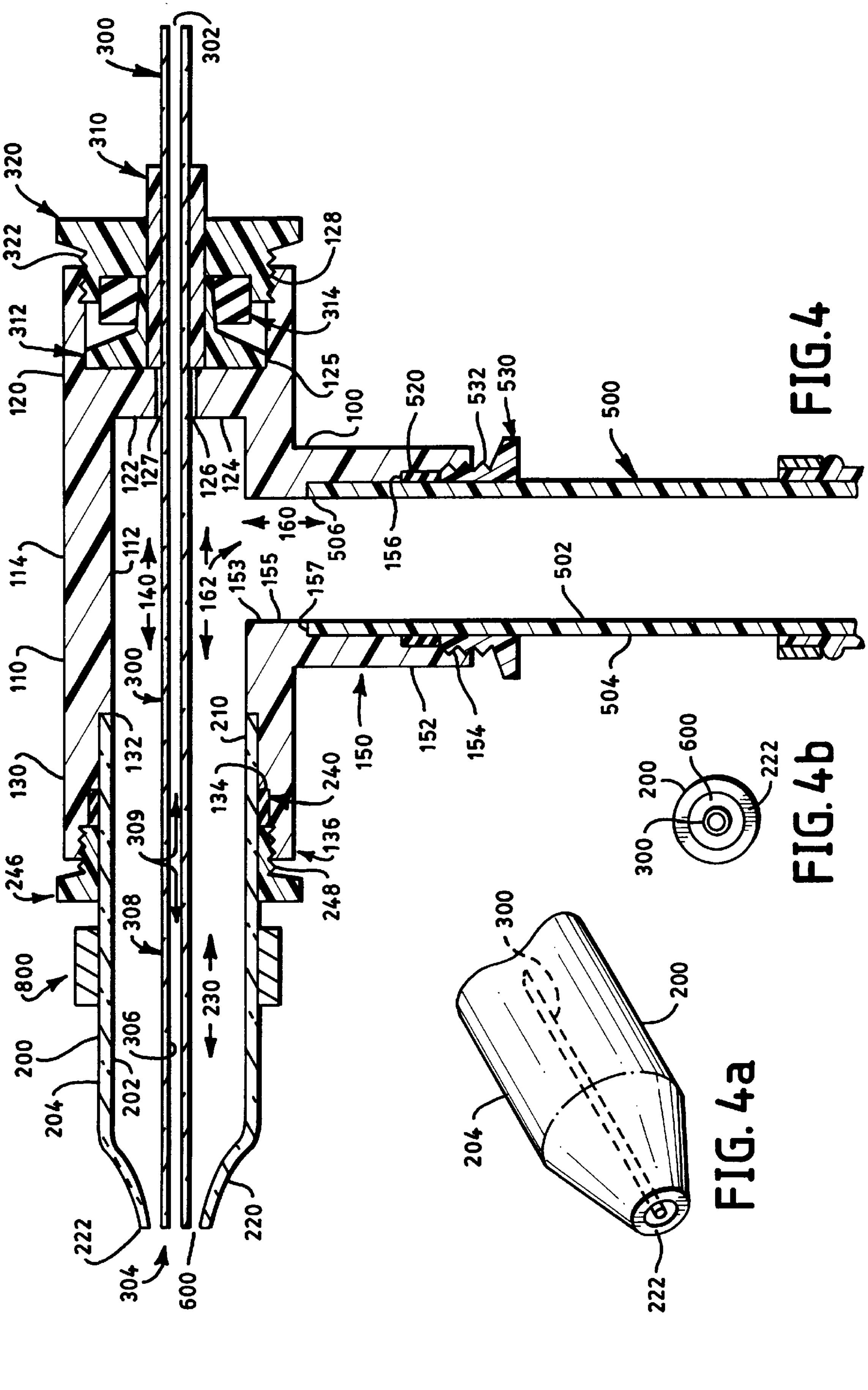
FIGS. 4, 4*a*, and 4*b* are a side, cross-sectional view of nebulizer constructed in accordance with the preferred embodiment of the invention, a view of the nebulizer tube at approximately 45°, and a view of the nebulizer tube as seen from the front, respectively.

There are three general positions possible for sample exit port 304 with respect to orifice 222; sample exit port 304 may extend beyond orifice 222 to a point outside nebulizer tube 200, it may be flush with orifice 222 or, it may be recessed with respect to orifice 222 to a point inside nebulizer tube 200. When sample exit port 304 is flush with orifice 222, as shown in FIG. 4, the two portions lie in the same plane and, viewed from the front, appear as two concentric rings with an area of free space between them. The area of free space between the interior surface 202 of forward gas expulsion end 220 and the outer cylindrical wall 308 of sample exit port 308 is the area through which gas under pressure is expelled and is defined as the gas annulus 600. For any given inner and outer diameters of orifice 222 and outer cylindrical wall 308, gas annulus 600 will have the same cross sectional area whether sample exit port 304 is flush with orifice 222 or extends beyond orifice 222 to a point outside nebulizer tube 200. The cross sectional area of gas annulus 600 will vary when sample exit port 304 is recessed with respect to orifice 222 and will be a function of linear translation as exit port 304 is recessed. In any event, the definition of gas annulus 600 shall remain the same. Two of the parameters upon which aerosol formation characteristics depend and can be adjusted are the cross sectional area of gas annulus 600 and the relative position of sample exit port 308 with respect to orifice 222.

By allowing a user of the apparatus to adjust the translational position of sample exit port 308 with respect to orifice 222 and to remove and interchange capillaries of various inner and outer diameters within the same nebulizer tube 200, experimentation is made easier, less expensive, and less time consuming. The interchangeability and adjustability of capillaries within a single nebulizer tube obviates the need for several one-piece nebulizers to achieve various desired effects and the need to disconnect the gas source required to create aerosol each time a nebulizer with different aerosol producing parameters is needed. Furthermore, the current device permits the user to interchange nebulizer tubes of various lengths, diameters, materials, and orifice diameter.

As a final feature, the nebulizer of the instant invention may be provided with an ICP adapter 800 which fits snugly, but removably around exterior surface 204. ICP adapter 800 may be used for mounting the nebulizer on the spray chamber of an ICP spectrometer. Adapter 800 may be used on any embodiment disclosed in this provisional application.

DESCRIPTION OF A SECOND EMBODIMENT

Figure 5:
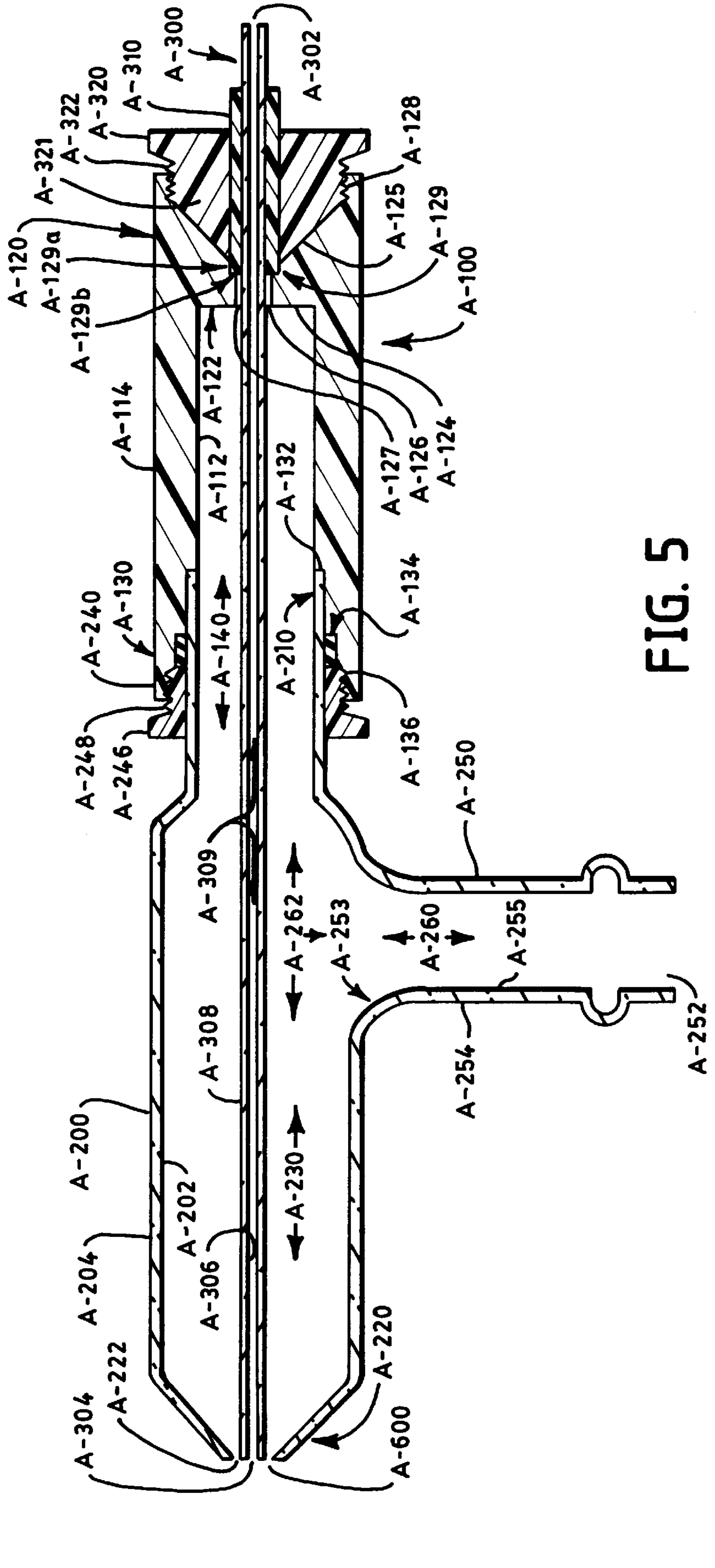
FIG. 5 is a side, cross-sectional view of a nebulizer constructed in accordance with a second embodiment of the invention. The nebulizer tube of FIG. 5 viewed from a 45° and from the front would appear the same as the depictions in FIGS. 4*a* and 4*b*.

A second specific embodiment has been developed in accordance With my invention and, for clarity and convenience, is discussed with frequent reference to the description of the preferred embodiment. The second embodiment of the invention operates on entirely the same principles as the preferred embodiment and is very similar in construction. In the second embodiment, however, the T-shape housing has been eliminated and, instead, a cylindrical housing is used. The gas conduit of the previous embodiment is integrally molded with the nebulizer tube to form a single, roughly T-shaped nebulizer tube. In all other respects, the nebulizer tube of the second embodiment is basically the same as that of the preferred embodiment. FIG. 5 does depict the nebulizer tube of the second embodiment as tapering down to a portion of constant radius at its rear end for insertion and sealable engagement with the front end of the housing and this in fact is how the device was actually constructed. However, nothing precludes the nebulizer tube in the second embodiment from having a constant radius at points other than its front end, nor does anything preclude the nebulizer tube of the preferred embodiment from tapering down to a reduced radius at its rear end. In fact, all such variations are regarded as within the scope of the invention as a whole.

Turning particularly to FIG. 5, there is depicted a second embodiment of my invention which comprises three main components: a cylindrical central housing A-100, a nebulizer tube A-200, and a central capillary A-300.

Central housing A-100 has a cylindrical interior wall A-112, an exterior wall A-114, a rear end A-120, and a front end A-130. A bore A-140 extends from rear end A-120 through front end A-130. Rear end A-120 contains a recessed capillary guide wall A-122 which has a front face A-124 and a rear face A-125. As constructed and depicted in FIG. 5, rear face A-125 is not a flat surface like in the preferred embodiment, but is rather shaped like a funnel for receiving a flexible cone-shaped ferrule portion A-321 to be described infra. Guide wall A-122 extends radially inward from cylindrical interior wall A-112 to a guide aperture A-126. Furthermore, at the forward end of funnel-shaped rear face A-125, and near guide aperture A-126, there is a compression sleeve seat A-129. Compression sleeve seat A-129 has a cylindrical side A-129*a* that is concentric with, but greater in radius than guide aperture A-126, and a flat front wall A-129*b* which has an outer radius equal to the radius of cylindrical side A-129*a* and an inner radius equal to the radius of guide aperture A-126. Guide aperture A-126 extends through guide wall A-122 from front face A-124 to flat front wall A-129*b* of compression sleeve seat A-129 and is bounded by a guide wall interior surface A-127. The portion of housing A-100 that extends behind rear face A125 of recessed guide wall A-122 contains rear end internal threads A-128 along interior wall A-112.

Front end A-130 is designed to removably receive and sealably engage nebulizer tube A-200. Front end A-130 has a nebulizer seat A-132, a nebulizer ferrule shoulder A134, and front end internal threads A-136. Nebulizer tube A-200, preferably constructed from glass, has an interior cylindrical surface A-202, an exterior surface A-204, a rear gas entrance end A-210, and a forward gas expulsion end A-220. Gas expulsion end A-220 is tapered downward and terminates in an expulsion orifice A-222. A channel A-230 communicates with expulsion orifice A-222 and extends rearward from expulsion orifice A-222 through rear gas entrance end A-210. Nebulizer tube A-200 is further provided with a nebulizer ferrule A-240 which is secured around exterior surface A-204 so that it cannot slide along surface A-204. Nebulizer securing nut A-246 is slidably received around exterior surface A-204. To install nebulizer tube A-200 into front end A-130 of housing A-100, rear gas entrance end A-210 is inserted into front end A-130 until rear gas entrance end A-210 comes into contact with nebulizer seat A-132 and nebulizer ferrule A-240 comes into contact with nebulizer ferrule shoulder A-134. To sealably secure nebulizer tube A-200 in place, nebulizer securing nut A-246, which has exterior threads A-248, is threaded into front end internal threads A-136 of front end A-130 until a seal sufficient to prevent pressurized gas from leaking through the contact points between nebulizer ferrule A-240 and exterior surface A-204 and nebulizer ferrule A-240 and nebulizer ferrule shoulder A-134 is created by the deformation of nebulizer ferrule A-240. A gas tight seal may also result between rear gas entrance end A-210 and nebulizer seat A-132, but all that is required is that gas cannot leak from the junction of nebulizer tube A-200 and front end A-130 of central housing A-100.

Extending substantially perpendicularly from exterior surface A-204 of nebulizer tube A-200 is an integral gas conduit A-250. Gas conduit A-250 has an open gas receiving end A-252, an open gas discharge end A-253, an exterior wall A-254, and an interior wall A-255. A bore A-260 extends through gas conduit A-250 from gas receiving end A-252 to gas discharge end A-253. Bore A-140 in housing A-100, channel A-230 extending through nebulizer tube A-200, and bore A-260 cooperate to form cavity A-262. Gas entrance conduit A-250 is designed to receive and sealably engage a gas line at its gas receiving end A-252. A gas line is fitted around, or into, gas receiving end and sealably secured thereto using any number of conventional and well-known means such as a hose clamp. Also, couplings widely used and well known by those familiar with the art could be used to secure a gas supply line to gas receiving end A-252. All that is necessary for the gas supply aspect of the invention to function properly is a gas tight seal between the source of gas and gas conduit A-250 so that gas being fed through the gas line and gas conduit A-250 cannot escape through the seal between gas conduit A-250 and the gas line.

Rear end A-120 of housing A-100 is adapted to receive central capillary A-300 through guide aperture A-126 in capillary guide wall A-122. Central capillary A-300 has a first sample intake port A-302, a second sample exit port A-304, a cylindrical inner wall A-306, and an outer cylindrical wall A-308. A sample channel A-309 extends from first sample intake port A-302 to second sample exit port A-304. Outer wall A-308 is provided with a cylindrical capillary compression sleeve A-310 which fits snugly around outer wall A-308, but nonetheless can be slid along outer wall A-308 when it is not being compressed. A capillary securing nut A-320 is slidably received around compression sleeve A-310. Capillary securing nut A-320 has at its forward end a flexible cone-shaped ferrule portion A-321 which is designed to be sealably received by funnel-shaped rear face A-125. When installation of central capillary A-300 is desired, nebulizer tube A-200 should be properly installed first. To install central capillary A-300, the end of capillary A-300 having second sample exit port A-304 is inserted into rear end A-120, through guide aperture A-126, and translated toward gas expulsion end A-220 of nebulizer tube A-200. When sample exit port A-304 is at the desired proximity with respect to orifice A-222, which is in alignment with guide aperture A-126, compression sleeve A-310 is slid forward until its forward portion comes to rest against front flat wall A-129*b* of compression sleeve seat A-129. Capillary securing nut A-320, which has external threads A-322, is then threaded into rear end internal threads A-128 of tube A-110 until ferrule portion A-321 is deformed and compressed onto capillary compression sleeve A-310, which in turn is compressed down onto capillary A-300, until capillary A-300 cannot be translated forward or backward and a gas tight seal is formed at capillary guide wall A-122 and between funnel shaped rear wall A-125 and cone-shaped ferrule portion A-321 so that gas in cavity A-262 cannot escape through guide aperture A-126 and out rear end A-120. To adjust the position of, or remove, central capillary A-300, capillary securing nut A-320 is threaded out of rear end internal threads A-128 to allow ferrule portion A-321 to release compression sleeve A-310 and permit translational motion between ferrule portion A-321 and capillary compression sleeve A-310. As with the preferred embodiment, there are three general positions possible for sample exit port A-304 with respect to orifice A-222; sample exit port A-304 may extend beyond orifice A-222 to a point outside nebulizer tube A-200, it may be flush with orifice A-222 or, it may be recessed with respect to orifice A-222 to a point inside nebulizer tube A-200. When sample exit port A-304 is flush with orifice A-222, the two portions lie in the same plane and, viewed from the front, appear as two concentric rings with an area of free space between them (Same as that shown in FIG. 4*b*). The area of free space between the interior surface A-202 of forward gas expulsion end A-220 and the outer cylindrical wall A-308 of sample exit port A-308 is the area through which gas is expelled under pressure and is defined as the gas annulus A-600. For any given inner and outer diameters of orifice A-222 and outer cylindrical wall A-308, gas annulus A-600 will have the same cross sectional area whether sample exit port A-304 is flush with orifice A-222 or extends beyond orifice A-222 to a point outside nebulizer tube A-200. The cross sectional area of gas annulus A-600 will vary when sample exit port A-304 is recessed with respect to orifice A-222 and will be a function of linear translation as exit port A-304 is recessed. In any event, the definition of gas annulus A-600 shall remain the same. Two of the parameters upon which aerosol formation characteristics depend and can be adjusted are the cross sectional area of gas annulus A-600 and the relative position of sample exit port A-308 with respect to orifice A-222.

The advantages of a device that permits a user to adjust these and other parameters were discussed at the end of the detailed description of the preferred embodiment. The operation of this second embodiment is in all material respects the same as that of the first embodiment except for differences specifically mentioned. One disadvantage of this embodiment as compared with the preferred embodiment is that when the user wishes to change the nebulizer tube, he or she must disconnect the gas line from the gas conduit and connect it to the replacement nebulizer tube.

The foregoing is considered to be illustrative only of the principles of the invention. Furthermore, since numerous modifications and changes will readily occur to those of ordinary skill in the art, it is not desired that the foregoing limit the invention to the exact construction and operation shown and described. Accordingly, all suitable modifications and equivalents may be resorted to that appropriately fall within the scope of the invention. Other embodiments therefore will occur to those skilled in the art and are within the scope of the following claims:

What is claimed is:

1. A pneumatic concentric nebulizer with an adjustable and replaceable central sample capillary comprising:

a central housing having an open rear end, an open front end, a bore extending from said rear end to said front end, and a gas entrance opening communicating with said bore, said gas entrance opening being adapted for gas-tight engagement with a source of pressurized gas for introducing pressurized gas into said housing;

a nebulizer tube having a rear gas entrance end, a forward gas expulsion end and an interior surface extending between said gas entrance and gas expulsion ends and defining a channel therebetween, said forward end terminating in a gas expulsion orifice;

nebulizer tube sealing means proximate to said front end of said housing for removably receiving and sealably engaging said nebulizer tube proximate its gas entrance end so that a gas tight seal is formed between said nebulizer tube and said housing when the apparatus is in use;

a central capillary having a sample intake port, a sample exit port, an outer wall, and an inner wall, said inner wall defining a sample channel that extends from said sample intake port to said sample exit port, said sample intake port being attachable to a source of sample to be nebulized;

capillary sealing means proximate to said rear end of said housing, said capillary sealing means being movable between an open position and a sealing position for slidably and removably receiving, and selectively sealably engaging, said capillary such that when said capillary sealing means are in the open position said sample exit port of said capillary may be received through said rear end of said housing and translated linearly forward within said housing toward said gas expulsion end of said nebulizer tube until a desired location for said sample exit port with respect to said gas expulsion orifice has been attained at which point said capillary sealing means can be moved into its sealing position to form a gas tight seal between said housing and said capillary so that when said nebulizer tube and said capillary are both sealably engaged by said housing, and pressurized gas is introduced into said housing through said gas entrance opening, the gas is expelled through said gas expulsion orifice of said nebulizer tube at a high enough velocity to create a low pressure system in the vicinity of said sample exit port of said capillary sufficient to draw sample from said capillary by free suction into the path of the exiting g as which in turn will nebulize the sample and propel it generally in the direction of the exiting gas.

2. The invention of claim 1 wherein said housing is substantially T-shaped and comprises a tube portion corresponding to the horizontal portion of the "T" and extending from said open rear end to said open front end, and further comprises a gas conduit depending from said tube portion which is in gas-tight fluid communication with said gas entrance opening and extends substantially perpendicularly from said tube portion to facilitate convenient connection of said housing to the source of pressurized gas.

3. The invention of claim 1 wherein said forward gas expulsion end of said nubulizer tube is tapered downward toward said orifice to form a substantially cone shaped nozzle.

4. The invention of claim 3 wherein the position of said sample exit port of said capillary is adjustable between positions beyond said gas expulsion orifice of said nebulizer tube and recessed with respect to said gas expulsion orifice to permit the user to attain various gas back pressures within said nebulizer tube and various nebulization effects.

5. The invention of claim 1 wherein said capillary sealing means is capable of receiving and sealably engaging capillaries of various inner and outer diameters.

6. A pneumatic concentric nebulizer with an adjustable and replaceable central sample capillary comprising:

a central housing having an open rear end, an open front end, and a bore extending from said rear end to said front end;

a nebulizer tube having a rear gas entrance end, a forward gas expulsion end and an interior surface extending between said gas entrance and gas expulsion ends and defining a channel therebetween, said forward end terminating in a gas expulsion orifice, said nebulizer tube further including an integral gas conduit depending therefrom which gas conduit is in fluid communication with said channel within said nebulizer tube and attachable to a source of pressurized gas so that pressurized gas can be introduced into said nebulizer tube;

nebulizer tube sealing means proximate to said front end of said housing for removably receiving and sealably engaging said nebulizer tube proximate its gas entrance end so that a gas tight seal is formed between said nebulizer tube and said housing when the apparatus is in use;

a central capillary having a sample intake port, a sample exit port, an outer wall, and an inner wall, said inner wall defining a sample channel that extends from said sample intake port to said sample exit port, said sample intake port being attachable to a source of sample to be nebulized;

capillary sealing means proximate to said rear end of said housing, said sealing means being movable between an open position and a sealing position for slidably and removably receiving, and selectively sealably engaging, said capillary such that when said capillary sealing means are in the open position said sample exit port of said capillary may be received through said rear end of said housing and translated linearly forward within said housing toward said gas expulsion end of said nebulizer tube until a desired location for said sample exit port with respect to said gas expulsion orifice has been attained at which point said capillary sealing means can be moved into its sealing position to form a gas tight seal between said housing and said capillary so that when said nebulizer tube and said capillary are both sealably engaged by said housing, and pressurized gas is introduced into said nebulizer tube through said integral gas conduit, the gas is expelled through said gas expulsion orifice of said nebulizer tube at a high enough velocity to create a low pressure system in the vicinity of said sample exit port of said capillary sufficient to draw sample from said capillary by free suction into the path of the exiting gas which in turn will nebulize the sample and propel it generally in the direction of the exiting gas.

7. The invention of claim 6 wherein said forward gas expulsion end of said nubulizer tube is tapered downward toward said orifice to form a substantially cone shaped nozzle.

8. The invention of claim 7 wherein said sample exit port of said capillary is movable between positions beyond said gas expulsion orifice of said nebulizer tube and recessed with respect to said gas expulsion orifice to permit the user to attain various gas back pressures within said nebulizer tube and various nebulization effects.

9. The invention of claim 6 wherein said capillary sealing means is capable of receiving and sealably engaging capillaries of various inner and outer diameters.

10. A pneumatic concentric nebulizer with an adjustable and replaceable central sample capillary comprising:

a central housing having an open rear end, an open front end, a bore extending from said rear end to said front end, and a gas entrance opening communicating with said bore, said gas entrance opening being adapted for gas-tight engagement with a source of pressurized gas for introducing pressurized gas into said housing;

a nebulizer tube having a rear gas entrance end, a forward gas expulsion end and an interior surface extending between said gas entrance and gas expulsion ends and defining a channel therebetween, said forward end terminating in a gas expulsion orifice;

nebulizer tube sealing means proximate to said front end of said housing for removably receiving and sealably engaging said nebulizer tube proximate its gas entrance end so that a gas tight seal is formed between said nebulizer tube and said housing when the apparatus is in use;

a central capillary having a sample intake port, a sample exit port, an outer wall, and an inner wall, said inner wall defining a sample channel that extends from said sample intake port to said sample exit port, said sample intake port being attachable to a source of sample to be pumped into said sample intake port, through said sample channel, and out said exit port to be nebulized;

capillary sealing means proximate to said rear end of said housing, said capillary sealing means being movable between an open position and a sealing position for slidably and removably receiving, and selectively sealably engaging, said capillary such that when said capillary sealing means are in the open position said sample exit port of said capillary may be received through said rear end of said housing and translated linearly forward within said housing toward said gas expulsion end of said nebulizer tube until a desired location for said sample exit port with respect to said gas expulsion orifice has been attained at which point said capillary sealing means can be moved into its sealing position to form a gas tight seal between said housing and said capillary so that when said nebulizer tube and said capillary are both sealably engaged by said housing, and pressurized gas is introduced into said housing through said gas entrance opening, the gas is expelled through said gas expulsion orifice of said nebulizer tube at a high enough velocity to nebulize and propel sample being pumped through said sample capillary into the path of the gas generally in the direction of the exiting gas.

11. The invention of claim 10 wherein said housing is substantially T-shaped and comprises a tube portion corresponding to the horizontal portion of the "T" and extending from said open rear end to said open front end, and further comprises a gas conduit depending from said tube portion which is in gas-tight fluid communication with said gas entrance opening and extends substantially perpendicularly from said tube portion to facilitate convenient connection of said housing to the source of pressurized gas.

12. The invention of claim 10 wherein said forward gas expulsion end of said nubulizer tube is tapered downward toward said orifice to form a substantially cone shaped nozzle.

13. The invention of claim 12 wherein the position of said sample exit port of said capillary is adjustable between positions beyond said gas expulsion orifice of said nebulizer tube and recessed with respect to said gas expulsion orifice to permit the user to attain various gas back pressures within said nebulizer tube and various nebulization effects.

14. The invention of claim 10 wherein said capillary sealing means is capable of receiving and sealably engaging capillaries of various inner and outer diameters.

15. A pneumatic concentric nebulizer with an adjustable and replaceable central sample capillary comprising:

a central housing having an open rear end, an open front end, and a bore extending from said rear end to said front end;

a nebulizer tube having a rear gas entrance end, a forward gas expulsion end and an interior surface extending between said gas entrance and gas expulsion ends and defining a channel therebetween, said forward end terminating in an expulsion orifice, said nebulizer tube further including an integral gas conduit depending therefrom which gas conduit is in fluid communication with said channel within said nebulizer tube and attachable to a source of pressurized gas so that pressurized gas can be introduced into said nebulizer tube;

nebulizer tube sealing means proximate to said front end of said housing for removably receiving and sealably engaging said nebulizer tube proximate its gas entrance end so that a gas tight seal is formed between said nebulizer tube and said housing when the apparatus is in use;

a central capillary having a sample intake port, a sample exit port, an outer wall, and an inner wall, said inner wall defining a sample channel that extends from said sample intake port to said sample exit port, said sample intake port being attachable to a source of sample to be pumped into said sample intake port, through said sample channel, and out said exit port to be nebulized;

capillary sealing means proximate to said rear end of said housing, said capillary sealing means being movable between an open position and a sealing position for slidably and removably receiving, and selectively sealably engaging, said capillary such that when said capillary sealing means are in the open position said sample exit port of said capillary may be received through said rear end of said housing and translated linearly forward within said housing toward said gas expulsion end of said nebulizer tube until a desired location for said sample exit port with respect to said gas expulsion orifice has been attained at which point said capillary sealing means can be moved into its sealing position to form a gas tight seal between said housing and said capillary so that when said nebulizer tube and said capillary are both sealably engaged by said housing, and pressurized gas is introduced into said nebulizer tube through said integral gas conduit, the gas is expelled through said gas expulsion orifice of said nebulizer tube at a high enough velocity to nebulize and propel sample being pumped through said sample capillary into the path of the gas generally in the direction of the exiting gas.

16. The invention of claim 15 wherein said forward gas expulsion end of said nubulizer tube is tapered downward toward said orifice to form a substantially cone shaped nozzle.

17. The invention of claim 16 wherein said sample exit port of said capillary is movable between positions beyond said gas expulsion orifice of said nebulizer tube and recessed with respect to said gas expulsion orifice to permit the user to attain various gas back pressures within said nebulizer tube and various nebulization effects.

18. The invention of claim 15 wherein said capillary sealing means is capable of receiving and sealably engaging capillaries of various inner and outer diameters.

* * * * *